(12) United States Patent
Heese et al.

(10) Patent No.: US 7,276,253 B2
(45) Date of Patent: *Oct. 2, 2007

(54) STABLE DRUG FORM FOR ORAL ADMINISTRATION WITH BENZIMIDAZOLE DERIVATIVES AS ACTIVE INGREDIENT AND PROCESS FOR THE PREPARATION THEREOF

(75) Inventors: Gerd-Ulfert Heese, Munich (DE); Herbert Jünger, Dachau (DE); Arnim Laicher, Sauerlach (DE); Claudio Lorck, Munich (DE); Thomas Profitlich, Munich (DE); Gerd Weiss, Munich (DE)

(73) Assignee: AstraZeneca AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 11/502,830

(22) Filed: Aug. 11, 2006

(65) Prior Publication Data

US 2007/0048380 A1    Mar. 1, 2007

Related U.S. Application Data (60) Division of application No. 10/665,081, filed on Sep. 16, 2003, now abandoned, which is a continuation of application No. 09/947,166, filed on Sep. 5, 2001, now Pat. No. 6,623,759, which is a continuation of application No. 09/219,985, filed on Dec. 23, 1998, now abandoned, which is a continuation of application No. PCT/EP97/03387, filed on Jun. 27, 1997.

(30) Foreign Application Priority Data

Jun. 28, 1996 (DE) .................. 196 26 045

(51) Int. Cl.
*A61K 9/14* (2006.01)
*A61K 9/16* (2006.01)
*A61K 9/20* (2006.01)
*A61K 9/24* (2006.01)
*A61K 9/28* (2006.01)

(52) U.S. Cl. .................. 424/472; 424/464; 424/471; 424/474; 424/480; 424/489; 424/490; 424/494; 424/472

(58) Field of Classification Search .............. None
See application file for complete search history.

(56) References Cited

U.S. PATENT DOCUMENTS

| | | | |
|---|---|---|---|
| 4,255,431 A | 3/1981 | Junggren et al. | 424/263 |
| 4,786,505 A | 11/1988 | Lovgren et al. | 424/468 |
| 4,853,230 A | 8/1989 | Lovgren et al. | 424/466 |
| 4,980,170 A | 12/1990 | Schneider et al. | 424/451 |
| 5,385,739 A | 1/1995 | Debregeas et al. | 424/494 |
| 5,417,980 A | 5/1995 | Goldman et al. | 424/464 |
| 5,601,843 A | 2/1997 | Gimet et al. | 424/475 |
| 5,698,225 A | 12/1997 | Gimet et al. | 424/475 |
| 5,753,265 A | 5/1998 | Bergstrand et al. | 424/474 |
| 5,817,338 A | 10/1998 | Bergstrand et al. | 424/468 |
| 5,900,424 A | 5/1999 | Källström et al. | 514/338 |
| 6,013,281 A | 1/2000 | Lundberg et al. | 424/468 |
| 6,365,184 B1 | 4/2002 | Depui et al. | 424/469 |

FOREIGN PATENT DOCUMENTS

| | | |
|---|---|---|
| EP | 0237200 | 9/1987 |
| EP | 0496437 | 7/1992 |
| EP | 0519144 | 12/1992 |
| EP | 0567201 | 10/1993 |
| WO | 9402140 | 2/1994 |
| WO | 9501783 | 1/1995 |
| WO | 9725064 | 7/1997 |

OTHER PUBLICATIONS

Überzogene Arzneiformen, by Bauer et al.; Wissenschaftliche Verlagsgesellschaft mbH, Stuttgart, 1998, pp. 88-89.

*Primary Examiner*—S. Tran
(74) *Attorney, Agent, or Firm*—White & Case LLP

(57) ABSTRACT

The invention relates to a stable medicament for oral administration which comprises
(a) a core which contains an active ingredient selected from Omeprazole, Lansoprazole and Pantoprazole, together with customary pharmaceutical adjuvants,
(b) an intermediate layer applied onto the core, and
(c) a gastric juice-resistant outer layer. The intermediate layer in (b) is formed as a reactive layer in which a gastric juice-resistant polymer layer material partially neutralized with alkali with cation exchange capacity is present.

Further, a method for the production of the stable medicament is disclosed.

23 Claims, 7 Drawing Sheets

Schematic layer construction according to the invention

STABLE DRUG FORM FOR ORAL ADMINISTRATION WITH BENZIMIDAZOLE DERIVATIVES AS ACTIVE INGREDIENT AND PROCESS FOR THE PREPARATION THEREOF

This application is a divisional of U.S. patent application Ser. No. 10/665,081, filed Sep. 16, 2003, now abandoned which is a continuation of U.S. patent application Ser. No. 09/947,166, filed Sep. 5, 2001, now U.S. Pat. No. 6,623,759, which is a continuation of U.S. patent application Ser. No. 09/219,985, filed Dec. 23, 1998, abandoned, which is a continuation of International Application PCT/EP97/03387, filed Jun. 27, 1997.

The present invention discloses a stable medicament for oral administration which comprises-one or more of the benzimidazole derivatives Omeprazole, Lansoprazole or Pantoprazole as an active ingredient as well as a method for its production.

It is known from EP 0 005 129 that Omeprazole (5-methoxy-2(((4-methoxy-3,5-dimethyl-2-pyridyl)methyl)-sulfinyl)-1H-benzimidazole functions as a potent inhibitor in the secretion of gastric acid. Omeprazole has proven itself in the therapy of duodenal ulcer, gastric ulcer, reflux esophagitis and Zollinger-Ellision syndrome. Parenteral and solid peroral medicaments are employed in this connection.

The following embodiments presented for Omeprazole apply in the same manner for Lansoprazole (2-(((3-methyl-4-(2,2,2-trifluoroethoxy)-2-pyridyl)methyl)-sulfinyl)-1H-benzimidazole) and Pantoprazole (5-difluoromethoxy-2-(((3,4-dimethoxy-2-pyridyl)methyl)-sulfinyl)-1H-benzimidazole).

The administration of a medicine per os is especially convenient because it can be carried out by patients practically anywhere and at any time without effort and unpleasant attendant phenomena. The oral administration inevitably leads to the fact that the medicament reaches the stomach at first. However, Omeprazole and its derivatives degrade very rapidly in the acidic environment of the stomach to ineffective compounds. For example, Omeprazole has a half-life of less than ten minutes in aqueous solution at pH values under 4. Therefore, solid peroral medicines (tablets, pellets, granulates) of Omeprazole and similar active ingredients must be completely protected against gastric juice.

The resorption of Omeprazole occurs in the upper duodenum whereby this active ingredient exhibits a pronounced first-pass-effect. Therefore, an as quick and complete release as possible of the active ingredient from the medicament after passage of the pylorus must be ensured in order to guarantee a sufficiently high bio-availability.

For this, Omeprazole is provided with a coating of enteric, i.e. gastric juice-resistant materials, which is insoluble in the acid environment of the stomach (ca. pH 1 to 3) on the one hand, but dissolves in the weakly acidic to weakly alkaline region of the duodenum (pH >5.5). It is known to introduce the extremely acid sensitive active ingredient Omeprazole into the core of a pellet formulation onto which one or more coating layers provided.

Frequently, Eudragit® L100 or L100-55 is used a layer material. Eudragit® L100 is a copolymer of methacrylic acid and methylmethacrylate in a certain ratio and is insoluble in an acidic environment, for example in the stomach, and therewith forms a considerably impermeable protective layer. Eudragit® L100-55 is a copolymer of methacrylic acid and ethylacrylate, whereby the ratio of the monomers is chosen in such a manner that it is insoluble at a pH <5.5, but is soluble at a pH above this. The reason for this essentially lies in the fact that the carboxyl side groups of the polymer are protonated in the acidic environment, and therewith, the polymer is non-charged as a whole. In the weakly acidic neutral and/or basic environment, for example in the intestine region, the carboxyl groups deprotonate whereby the polymer obtains negative charges. It is then water-soluble whereby the active ingredient is released.

However, Eudragit® cannot be applied directly onto the Omeprazole core because the carboxyl groups in the coating layer degrade the Omeprazole which also presents problems in the production and storage of the medicament. Even small amounts of degradation products already lead to unambiguous color changes, and therewith to loss of quality, which no longer allow administration to patients under certain conditions. The storage problems are intensified when moisture penetrates into the active ingredient-containing core through hair-line cracks and other defects in the coating layer.

Gastric juice-resistant coatings of the above-mentioned polymers which are separated from the active ingredient-containing core by an inert isolation layer are suitable for the protection of solid, peroral medicaments with Omeprazole, Lansoprazole or Pantoprazole as an active ingredient against unfavourable storage conditions and against gastric juice in oral ingestion. Additionally, it has also been proven to be appropriate to stabilize the active ingredient-containing core by addition of an alkaline reacting substance. On the other hand, a sufficiently fast release in the intestine must be ensured.

BACKGROUND ART

DE 1 204 363 describes a medicament comprising a core with various layers applied thereto. The first (inner most) layer is soluble in the stomach, but insoluble in the intestine. The second protective layer is water soluble (independent of the pH value) and the third (outer most) protective layer is a gastric juice-resistant coating. However, this formulation is not suitable for Omeprazole because it only dissolves slowly in the intestine. However, a fast dissolution in the intestine is essential for the desired bio-availability.

EP 0 247 983 discloses a pharmaceutical agent for oral administration which comprises Omeprazole as an effective component. The core material contains Omeprazole together with an alkaline reacting compound or an Omeprazole salt, optionally together with an alkaline reacting adjuvant. Intermediate layers which form a separation layer between the alkaline reacting core and an outer layer of a gastric juice-resistant coating comprise water-soluble tablet carrier mediums or tablet carrier mediums quickly disintegrating in water or polymeric, water-soluble, film-forming substance mixtures which optionally contain buffering, alkaline compounds and which should capture protons penetrating from the outside. Aside from its water-solubility, the layer material is chemically and physically inert.

However, with use of an alkaline buffering substance, such as sodium acetate for example, this freely diffuses into the intermediate layer and penetrates into the outer gastric juice-resistant layer. The increase of the pH value associated therewith can favour the penetration of moisture through the enteric layer as a result of the increasing solubility. This means that the danger exists with the penetration of higher concentrations of protons that these reach the core and destroy the Omeprazole there. This last phenomena can easily occur especially when the outer gastric juice-resistant layer possesses faults as a result of imperfections which can arise in production, physical load or through ageing manifestations in storage.

EP 0 519 144 describes Omeprazole pellets consisting of an inert pellet core which is coded with the micronized active ingredient and is subsequently coated with a gastric juice-resistant layer. The following adjuvants, dispersed in water, are employed for coating the core with Omeprazole: hydroxymethylcellulose (HMC), water-free lactose, L-hydroxypropylcellulose (L-HPC), sodium lauryl sulfate, disodium hydrogen phosphate dihydrate. Hydroxypropylmethylcellulose phthalate (HPMCP) is used as a gastric juice-resistant coating. In this method, a possible reaction of the Omeprazole with the polymer is not excluded which can especially lead to a deteriorated storage stability.

EP 0 496 437 encompasses pellet cores and/or tablets which contain Omeprazole or an alkaline salt of Omeprazole together with an alkaline reacting compound (buffer) and which are coated with a layer of water-soluble, film-forming adjuvants which preferably react alkaline (buffer) as well as with a gastric juice-resistant outer film.

EP 0 239 200 uses basic magnesium salts and/or basic calcium salts for stabilizing benzimidazole derivatives with Omeprazole as typical representative.

According to this, numerous efforts were undertaken in the production of Omeprazole medicines which prevent the discoloration of the active ingredient, which considerably reduce the chemical degradation of Omeprazole, which prevent the degradation of the active ingredient in acidic gastric juice, but should simultaneously release the active ingredient as quickly as possible in the environment of the small intestine.

Object of the present invention is to provide an improved medicament as compared to the state of the art suitable for oral administration which comprises Omeprazole, Lansoprazole and/or Pantoprazole as an active ingredient, optionally in combination with further pharmaceutically effective substances, and which possesses-excellent stability in extended storage and under chemico-physical load. In particular, the penetration of acidic gastric juice into faults, cracks, chips or any other imperfections of the coating layer into the core layer should be avoided with the medicament according to the invention and the degradation of the acid-label active ingredient should be prevented therewith.

The medicament according to the invention guarantees a very high medicament security which above all should also be provided if unfavourable conditions arise in the course of the manufacturing process of the medicament as well as in the handling of the same and/or its packaged form by patients.

At the same time, it is necessary that the medicament quickly releases the active ingredient in the small intestine after passage through the stomach. Additionally, the degradation of the medicament should prevent the occurrence of discoloration of the active ingredient.

The above problem is solved according to the invention by a stable medicament for oral administration which (a) comprises a core which contains an active ingredient selected from Omeprazole, Lansoprazole and Pantoprazole together with customary pharmaceutical adjuvants, (b) an intermediate layer applied to the core, and (c) a gastric juice-resistant outer layer, characterized in that a reactive intermediate layer of gastric juice-resistant polymer layer material-partially neutralized with alkali with cation exchange capacity is present in (b).

Furthermore, subject-matter of the invention is a method for the production of the above-mentioned medicament, whereby (a) a molded article is formed as the core which contains an active ingredient selected from Omeprazole, Lansoprazole and Pantoprazole, together customary pharmaceutical adjuvants, (b) an intermediate layer is applied to the molded article, and (c) the coated molded article is laminated with a gastric juice-resistant layer, and the method is characterized in that a reactive intermediate layer of a gastric juice-resistant polymer-coat material partially neutralized with alkali with cation exchange capacity is applied in (b).

Preferred embodiments of the invention are given in the dependant claims.

Figure 1:
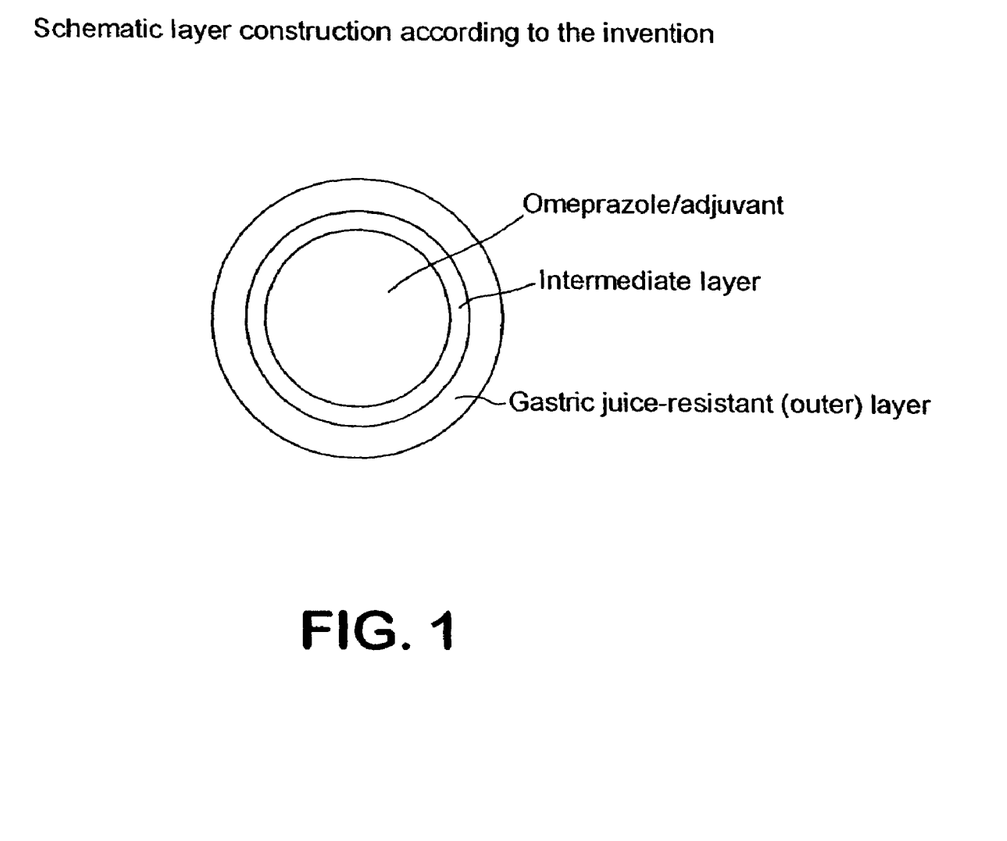
FIG. 1 shows a schematic layer construction according to the invention.

The layer construction of the medicament according to the invention is schematically given in FIG. 1.

The core of the medicament according to the invention encompasses the active ingredient Omeprazole, Lansoprazole or Pantoprazole individually or combinations thereof together with customary auxiliary substances. For the stability of the medicament according to the invention it is not necessary and is also not preferred that the core of the active ingredient is formulated together with an alkaline reacting compound. It is also not necessary for an, alkaline salt of the active ingredient be employed.

As the pharmaceutical adjuvants for the core, fillers such as mannite, hydroxypropylcellulose, microcrystalline cellulose and water-free lactose are especially suitable. Additionally, it has be shown that advantageous stability effects can be obtained by using a specific combination of mannite and hydroxypropylcellulose as a non-alkalizing adjuvant in the core.

The core can also comprise tensides which are selected in the suitable manner from sodium lauryl sulfate, sorbitan fatty acid ester and polyoxyethylene sorbitan fatty acid ester.

The core of the medicament according to the invention can be formed as a molded article. Preferred molded articles are pellet cores, tablets microtablets or granulates.

Figure 2:
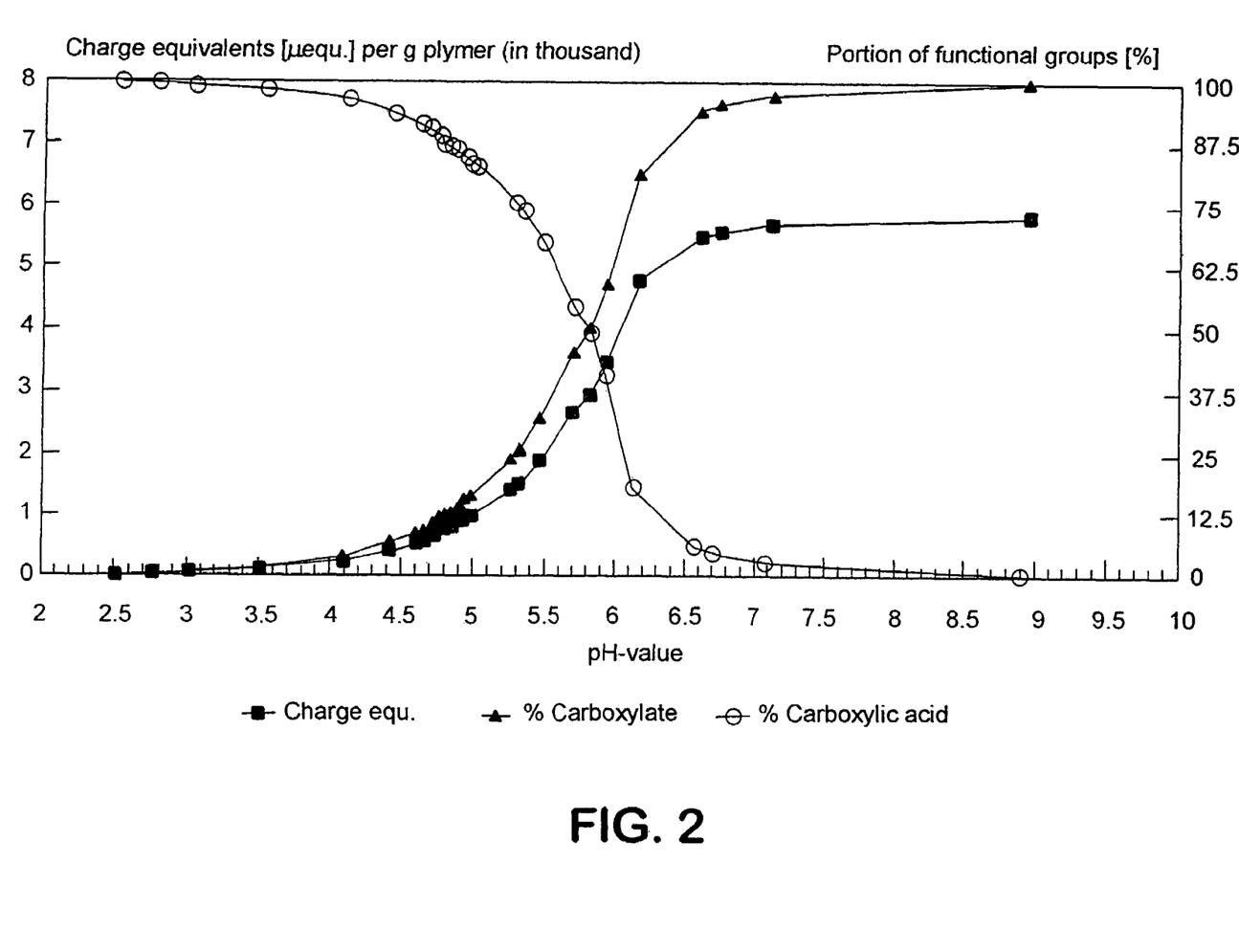
FIG. 2 graphically describes the effect of pH on charge equivalents and functional groups.

The molded articles are coated with an intermediate layer. This intermediate layer preferably has a layer thickness of approximately 5 to 30 µm. It forms a mechanical as well as chemical barrier to the core. Thereby, it is necessary that the intermediate layer be present in an intact film. The polymer of the intermediate layer amounts to approximately 3 to 5% by weight of the core weight. The intermediate layer comprises a gastric juice-resistant polymer layer material which was adjusted with alkali to pH range of 5.5 to 7.0, preferably 5.5 to 6.5. With these pH values, not all protons of the acidic functions of the polymer material are exchanged; the material is merely partially neutralized. As emerges from FIG. 2, less than 40% of the carboxyl functions in the case of Eudragit® are present at a pH of 5.5. Despite this, a combination of Eudragit® partially neutralized to pH 5.5 with Omeprazole is unexpectedly stable even under intensive storage conditions (see Example 2). At pH 7.0, ca. 97% of the carboxyl functions of Eudragit® are neutralized (see FIG. 2).

As alkali substances, substances are to be understood whose solutions demonstrate alkaline reactions with water (Römpps Chemistry Encyclopaedia, 8th Edition, 1979). In this connection, hydroxides of alkali metals, especially sodium and potassium, but also hydroxides of the earth alkali metals are primarily among these. Hydroxides of the alkali metals, especially sodium hydroxide, are preferred according to the invention.

In the partial neutralization, protons of the acidic functions are fixed through the polymer chains of the coat material, for example carboxyl groups, are partially replaced by alkali metal ions for example as counter-ions. The polymer layer material modified in this manner is no longer physico-chemically inert in the presence of protons, but rather, is reactive because it now possess cation exchange capacity. This means that when moisture and especially acidic gastric juice penetrates into cracks, faults, chips or other imperfections through the outer layer of the medicament according to the invention, the penetrating protons are captured and are exchanged by harmless alkali metal ions. A further aspect of the reactive principal of the intermediate layer material is demonstrated by the fact the intermediate layer is transformed at these places into a gastric juice-resistant barrier; it possess a "self-repair-mechanism" to a certain degree. Practical tests have shown that with contact of the intermediate layer with an acidic medium forms a gel-like substance which not only captures protons but also forms a flexible mechanical barrier which prevents the further penetration of moisture and/or acid medium. The partial neutralization of the polymer material for the reactive intermediate layer to a pH range 5.5 to 6.5 is especially preferred because a gastric juice-resistant barrier already forms when only few protons penetrate through the outer layer; on the other hand, the Omeprazole core is still sufficiently stable.

Thereby, a clearly improved stability behaviour of the claimed medicament in extended storage and under chemico-physical load is also obtained.

Buffering and/or alkalizing additives in the intermediate layer as proposed in EP 0 247 983 are no longer necessary and can even be damaging because they increase solubility of the intermediate layer and reduce its protective function. This nearly contradicts the "self-repair-mechanism" according to the invention; namely, the more basic equivalents that are present in the intermediate layer, the more protons must penetrate from the outside so that the "self-repair-mechanism" of the reactive layer has a quick effect.

Eudragit® L100-55, Eudragit® L100 produced from Röhm-Pharma, Germany, as well as hydroxypropylmethyl-cellulose phthalate (HPMCP) and cellulose acetate phthalate (CAP) which, as described above, are partially neutralized with alkali before use as an intermediate layer, i.e. before spraying of the same, are suitable as preferred substances for the intermediate layer. Particularly preferred is Eudragit® L100-55 obtainable world-wide as a commercial product.

The intermediate layer can contain customary additives, for example an emollient. Preferably, triethyl citrate, acetyl-triethyl citrate, acetylated monoglycerides, propylene glycol and polyethylene glycols are preferably suitable fore this.

The coated molded articles, i.e. the core and the intermediate layer, are then coated with an outer layer for the production of the medicament according to the invention. The outer layer represents a customary enteric; gastric juice-resistant layer. In this connection, commercial, aqueous polymer dispersions, such as polymethacrylates, for example Eudragit® L100-55 (Röhm Pharma), and coating CE 5142 (BASF) are suitable as materials. Additionally, polymers can also be used for formation of the gastric juice-resistant layer which are soluble in organic solvents. For example, phthalates (cellulose acetate phthalate, hydtoxypropylmethyl cellulose phthalate) are to be named as suitable materials. Additionally, the outer layer of the medicament according to the invention can contain antiblocking agents, dispersion agents, pigments and colorants. A suitable antiblocking agent is talcum for example.

In comparison to conventional medicinal forms with an inert intermediate layer, it was surprisingly determined that the inventive combination of enteric outer layer and reactive intermediate layer shows an accelerated dissolution behaviour in artificial intestinal fluid (pH ca. 5.8). This effect not only allows a very quick release of the active ingredient in the weakly acidic to weakly alkaline environment of the small intestine, and therewith an excellent bio-availability, but also permits improved medicament security because the enteric outer layer can be strengthened without retarding a desired quick release. Thereby, not only can the gastric juice-resistance be improved, but also the medicament stability especially under unfavourable storage conditions. Hence, the thickness of the gastric juice-resistant outer layer of the medicament according to the invention amounts to 2.0 to 60 µm (ca. 10 to 50% weight with respect to the core), preferably 30 to 60 µm.

In an advantageous embodiment of the invention, the reactive intermediate layer consists of partially neutralized Eudragit® L100-55 at a pH value of 5.5 to 7.0, preferably 5.5 to 6.5, and the outer layer consists of commercial Eudragit® L100-55 (pH ca. 2 to 3). The pH transition between outer layer and intermediate layer does not necessarily have to be discontinuous, but rather, can also be formed as a gradient, This can be obtained if several thin Eudragit layers are applied from inside to outside each of which was partially, neutralized to a decreasing pH value.

The reactive intermediate layer as well as the gastric juice-resistant outer layer can can be formed as a plurality of single layers.

The present invention further comprises a method for the production of a stable medicament for oral administration which comprises Omeprazole, Lansoprazole and/or Pantoprazole as an active ingredient.

According to the method of the invention, the active ingredient and adjuvants, such as mannite, hydroxypropyl-cellulose and sodium lauryl sulfate, are moistened together with a suitable solvent, preferably isopropanol, granulated and worked to the desired molded articles (for example pellets, granulates, tablets) according to customary methods. The molded articles are subsequently laminated with an aqueous dispersion consisting of a gastric juice-resistant substance partially neutralized with alkali to a pH value of ca. 5.5 to ca.7.0, preferably Eudragit® L100-55, as well as antiblocking agent and/or emollient, such as talcum and triethyl citrate, in a fluidized bed apparatus for example under formation of the intermediate layer with cation exchange activity. A quality product corresponding to Eudragit® L100-55 is also commercially obtainable as a finished suspension under the designation Eudragit® L30D-55. Subsequent to this, the coating occurs with a gastric juice-resistant substance (for example Eudragit® L100-55), talcum and an emollient (such as triethyl citrate) for formation of the enteric outer layer of the medicament according to the invention.

The production of pellets which are filled in gelatine capsules in an amount sufficient for the desired active ingredient dose is preferred.

Aside from the pellets containing the mentioned benzimidazole compounds, the capsule formulations produced in this manner can also contain other active ingredients. Preferable is a combination of Diclofenac- and Omeprazole-containing pellets. The Diclofenac-containing pellets are preferably produced according to the method of the invention, i.e. they also contain a reactive intermediate layer. However, they can also be produced by known methods, such as disclosed, in EP 0 348 808 for example. In a further embodiment, the Diclofenac-containing pellets are present as a mixture of gastric juice-resistant coated pellets and retarded permeable pellets which are first released in lower intestinal sections.

Combinations of non-steroidal inflammation inhibitors and analgesics are known. Thus, EP 0 527 887 names the combination of Diclofenac (o-(2,6-dichloroanilino)phenyl acetic acid), a highly effective NSAID (Non-Steroidal Anti-Inflammatory Drug), with Misoprostol, for example, which is employed for the treatment of painful inflammation diseases under the trade name Arthrotec®, Heumann Pharma GmbH, Germany. The prostaglandin derivative Misoprostol serves in this connection for prevention of NSAID-associated ulcer diseases.

The solid combination of Diclofenac and Omeprazole has a number of advantageous in long-term treatment of pain/inflammation. Thus, a combination of Diclofenac with Omeprazole maintains a low ulcer rate in patients who have a high risk for the development of gastrointestinal ulcers and who require treatment with an NSAID at the same time (ulcer prevention). Furthermore, this combination attains high ulcer healing rates in connection with sufficient pain relief (therapy). Patient compliance can be considerably increased as a result of the high effectiveness and good tolerance of the combination partners in connection with a single daily administration.

The capsule formulation which are suitable for direct administration per os comprise 25 to 200 mg, preferably 75 to 150 mg, Diclofenac and 10 to 40 mg, preferably 10 or 20 mg, Omeprazole as a unit dose in the pellets according to the invention.

The advantages of the medicament according to the invention with respect to Omeprazole and other benzimidazole-containing medicines of the art particularly exist in the fact that when any imperfections in the outer layer are present through which moisture upon storage or acidic gastric juice after peroral administration may penetrate into the core layer, the reactive intermediate layer not only captures protons but is additionally retransformed into a gastric juice-resistant layer material. Through this "self-repair-mechanism", a gel-like layer is formed which is able to prevent the penetration of moisture and acid into the core of the medicament. In case that no penetration of gastric juice occurs, the intermediate layer remains soluble. Unexpectedly, the combination of enteric outer layer and the active intermediate layer additionally shows an improved dissolution behaviour in artificial intestinal fluid which infers a correspondingly good dissolution behaviour in the small intestine.

The invention is more closely illustrated by the following examples without limiting the invention to said examples.

EXAMPLE 1

In Vitro Tests for Chemical/physical Stability of the Medicament According to the Invention: Trituration of Omeprazole and Intermediate Layer Material:

Storage experiments with trituration of Omeprazole and various treated intermediate layer materials were carried out over 32 days at 40° C. and 75% relative humidity (r.H). Subsequently, the degree to which the active ingredient Omeprazole (residual content in % by weight) remains stable, the percentage of degradation products arising (area-% from purity chromatogram) and the degree to which discoloration occurred were examined with HPLC. In this connection, Omeprazole with a non-pre-treated enteric coat material used for formation of gastric juice-resistant coatings (HPMCP, batch 1a, and Eudragit® L100-22, charge 1b, pH 0.2-3) and Omeprazole with a pre-treated enteric layer material (Eudragit® L100-55) according to the invention were triturated and stored open in Petri dishes under the given conditions. The pre-treated Eudragit® L100-55 was previously partially neutralized with sodium hydroxide to pH 5.5 (batch 1c) and pH 7.0 (batch 1d).

The results are reproduced in Table 1. The given values correspond to the average of 3 sample preparations. The discoloration is given as a color value according to "*Taschenlexikon der Farben*", A. Kornerup and J. H. Wauscher, Muster-Schmidt Publishers, Zürich, Göttingen, 3rd Edition, 1981.

TABLE 1

| Trituration | | Omeprazole content percent by weight | | Degradation product area-% | | Color value (standard - color table) | | |
|---|---|---|---|---|---|---|---|---|
| Batch (1:1) | Omeprazole + ... | after production | after 32 days | after production | after 32 days | after production | | after 32 day |
| | | | | Reference example | | | | |
| 1a | HPMCP | 100 | ⇨ 85 | <0.1 | ⇨ 7.0 | 5A1-2 (white-pale-orange) | ⇨ | 7C5 (brown) |

TABLE 1-continued

| Batch | Trituration Omeprazole + ... (1:1) | Omeprazole content percent by weight after production | | after 32 days | Degradation product area-% after production | | after 32 days | Color value (standard - color table) after production | | after 32 day |
|---|---|---|---|---|---|---|---|---|---|---|
| 1b | Eudragit L 100-55 pH 2–3 | 100 | ⇨ | 97 | <0.1 | ⇨ | 0.99 | 4A2 (pale light yellow) | ⇨ | 6B4 (brown-orange) |
| | | | | | according to invention | | | | | |
| 1c | Eudragit L 100-55 pH 5.5 | 100 | ⇨ | 97 | <0.1 | ⇨ | 0.25 | 1A1-2 (white- pale light yellow) | ⇨ | 12B2 (pale light grey) |
| 1d | Eudragit L 100-55, pH 7.0 | 100 | ⇨ | 98 | <0.1 | ⇨ | 0.25 | 1A1-2 (white- pale light yellow) | ⇨ | 11C2 (pale light grey) |

It is deduced from the column "Omeprazole content" that the active ingredient remains considerably more stable with use of partially neutralized, gastric juice-resistant polymer material according to the invention that in a trituration with a customary enteric substance which possess up to 100% free carboxyl groups. Thus, after 32 days storage under the named conditions, according to the invention only 2 or 3% of the active ingredient Omeprazole is degraded. In contrast, Omeprazole degradation up to 15% by weight is determined when using the customary enteric layer material HPMCP of the art in the present trituration experiments after 32 days. Additionally, no clear Omeprazole degradation (3% by weight) is demonstrated with use of non-neutralized Eudragit.

Instead, clear differences result in a comparison of the content of an Omeprazole degradation product appearing in the HPLC-chromatogram with use of partially neutralised Eudragit (pH 5.5 and 7.0) according to the invention with commercial Eudragit (pH 2 to 3) (see the column "Degradation Product"). Thus, according to the invention, hardly any degradation product is found after 32 days (0.25 area-% in both batches), whereas ca. 0.99 area-% in the presence of commercial Eudragit (pH 2 to 3) and even ca. 7% degradation product in the presence of a customary layer material (HPMCP) are present. This result is confirmed by the color comparison (see the column "color-value"). Neither the brown product of batch 1a nor the brown-orange product of batch 1b are still capable of being sold. In contrast, the treated products according to the invention (batches 1c and d) demonstrate a considerably lesser color change.

The above experiments prove that in the presence of high humidity and high temperature (intensified stability test) the partially neutralized layer material in the saturated state also functions protectively on the active ingredient Omeprazole.

In contrast, customary enteric layer material, which has up to 100% free COOH-groups, not only demonstrates no such protective effect, but also causes a clear degradation of the active ingredient.

EXAMPLE 2

Stability of Pellet Formulations:

In a further series of experiments, the medicament according to the invention was compared with the state of the art (EP 0 247 983). For this, various colored batches were produced which have a three-layer construction:

core, with the active ingredient Omeprazole in the presence of an alkaline buffering substance ($Na_2HPO_4$, according to the state of the art) and without alkaline buffering substance (according to the invention).

intermediate layer either consisting of a enteric layer material partially neutralized with alkali to a pH 6.0 and/or 7.0 according to the invention or inert layer material which contains sodium acetate as a buffering substance according to the state of the art. The reference example contains non-neutralized enteric layer material and sodium acetate as a buffering substance.

Outer layer of Eudragit L 100-55.

Additionally, a medicament was tested in the series of experiments in which the intermediate layer was omitted.

The respective pellet batches were stored open in a Petri dish for a week and 20 days at 40° C. and 75% relative humidity (r.H). Subsequently, the Omeprazole content and/or the appearance of degradation product was determined with HPLC. The values compiled in Table 2 represent the average of 3 sample preparations.

TABLE 2

| | | Omeprazole content percent by weight storage conditions 40° C./75% rel. Humidity storage duration | | | | Degradation product of Omeprazole area-% | | |
|---|---|---|---|---|---|---|---|---|
| | Batch Formula | after prod. | 1 Week | 20 days | after prod ... | | 1 Week |
| | | according to the invention | | | | | | |
| 2a | Omeprazole-core + adjuvant*, IL.: 3% E. L 100-55 pH 7.0 gjr: 30% E. L 100-55 | 100 | ⇨ | 92 | ⇨ | 84 | <0.4. | ⇨ | n.d. |

TABLE 2-continued

| Batch | Formula | Omeprazole content percent by weight storage conditions 40° C./75% rel. Humidity storage duration | | | Degradation product of Omeprazole area-% | |
|---|---|---|---|---|---|---|
| | | after prod. | 1 Week | 20 days | after prod . . . | 1 Week |
| 2b | Omeprazole-core + adjuvant*, IL.: 3% E. L 100-55 pH 6.0 gjr: 30% E. L 100-55 | 100 ⇨ | 93 ⇨ | 80 | <0.4 ⇨ | 2 |
| | Prior art | | | | | |
| 2c | Omeprazole-core + adjuvant*, IL.: 3% HPMC + NaOAc gjr: 30% E. L 100-55 | 100 ⇨ | 89 ⇨ | 66 | <0.4 ⇨ | 5 |
| 2d | Omeprazole-Core + Adjuvant*, IL.: 3% HPMC gjr: 30% E. L 100-55 | 100 ⇨ | 83 ⇨ | 57 | <0.4 ⇨ | 10 |
| 2e | Omeprazole-Core + Adjuvant*, keine IL. gjr: 30% E. L 100-55 | 100 ⇨ | 84 ⇨ | 54 | <0.4 ⇨ | 10 |
| | Reference example | | | | | |
| 2f | Omeprazole-Core + Adjuvant* + Na$_2$HPO$_4$ IL.: 3% HPMCP + NaOAc gjr: 30% HPMCP | 100 ⇨ | 73 ⇨ | 41 | <0.4 ⇨ | 16 |

*Adjuvant: Mannite, HPC, sodium lauryl sulfate
IL: Intermediate layer
E: Eudragit (percent by weight with respect to the core)
gjr: gastric juice-resistant (layer) (percent by weight with respect to the core)
n.d. = not determined In comparison with the state of the art, a clearly more stable administration form is obtained according to the invention. The pellets according to the invention still have 93% by weight of the active ingredient Omeprazole in an intact form after one week and 80% by weight of the active ingredient Omeprazole in an intact form after 20 days under the described intensified storage condition. Even after 4 weeks storage, an Omeprazole content of 67% by weight was determined according to the invention (not represented in the Table). In contrast, the Omeprazole content in medicament not according to the invention, i.e. those

- with an intermediate layer of HPMC and NaOAc
- with an intermediate layer of HPMC
- without an intermediate layer
- with an intermediate layer HPMCP and NaOAc merely amount to 66, 57, 54 and 41% by weight after 20 days.

EXAMPLE 3

"Self-Repair-Mechanism" of the Reactive Intermediate Layer:

Pellets with the following construction were compared:
- without intermediate layer (so-called pellet core)
- with the reactive intermediate layer according to the invention
- with an inert intermediate layer of HPMC (reference example)

For better judgement of the "self-repair-mechanism", the pellets were not provided with the outer enteric coat. All pellet types were tested in artificial gastric juice (pH 1.2) in a release model of the European Pharmacopoeia (basket). The intermediate layer was partially neutralized to pH 7.0, the upper limit of the preferred range.

The results (pellet cores without intermediate layer: not shown) are summarized in the following Table 3:

TABLE 3

| | Intermediate layer according to the invention Eudragit ® L100-55, pH 7.0, partially neutralized | | | | | | | | Reference example (HPMC) | |
|---|---|---|---|---|---|---|---|---|---|---|
| | 5% Intermediate layer 3a | | 10% Intermediate layer 3b | | 15% Intermediate layer 3c | | 20% Intermediate layer 3d | | 20% Intermediate layer 3e | |
| Time Batch (min) | Pellets discolored (%) | Color of the medium | Pellets discolored (%) | Color of the medium | Pellets discolored (%) | Color of the medium | Pellets discolored (%) | Color of the medium | Pellets discolored (%) | Color of the medium |
| 1 | 10 | light yellow | 0 | colorless | 0 | colorless | 0 | colorless | 10 | light yellow |
| 5 | 50 | green-yellow | 0 | colorless | 0 | colorless | 0 | colorless | 100 | brown |
| 10 | 80 | brownish | 5 | pale yellow | 0 | colorless | 0 | colorless | | |

TABLE 3-continued

| | Intermediate layer according to the invention Eudragit ® L100-55, pH 7.0, partially neutralized | | | | | | | | Reference example (HPMC) | |
|---|---|---|---|---|---|---|---|---|---|---|
| | 5% Intermediate layer 3a | | 10% Intermediate layer 3b | | 15% Intermediate layer 3c | | 20% Intermediate layer 3d | | 20% Intermediate layer 3e | |
| Time Batch (min) | Pellets discolored (%) | Color of the medium | Pellets discolored (%) | Color of the medium | Pellets discolored (%) | Color of the medium | Pellets discolored (%) | Color of the medium | Pellets discolored (%) | Color of the medium |
| 20 | 100 | brown | 30 | yellowish | 5 | pale yellow | 5 | pale yellow | | |
| 30 | | | 50 | green-yellow | 30 | yellowish | 5 | pale yellow | | |
| 50 | | | 70 | green-brown | 50 | green-yellow | 10 | light yellow | | |
| 70 | | | 80 | brownish | | | 10 | light yellow | | |
| 90 | | | | | | | | | | |
| 100 | | | 100 | brown | 70 | green-brown | 10 | light yellow | | |
| 120 | | | | | 80 | brownish | 30 | yellowish | | |

According to these results, pellets without intermediate layer (as comparison) completely dissolve within 2 minutes. The release medium has a strong brown coloration.

In contrast, pellets with the reactive intermediate layer according to the invention remain intact as a function of the layer thickness (up to 20% with respect to the core) of the intermediate layer up to a maximum of 120 minutes. The release medium-only has a slight discoloration.

Pellets with a customary inert intermediate layer according to the state of the art (reference example) with maximum layer thickness of the intermediate layer also completely dissolved within 5 minutes. The release medium has a strong brown discoloration.

These experiments proved a measurable protective mechanism with the intermediate layer according to the invention as opposed to pellets with an intermediate layer according to the state of the art. This protection mechanism brings about the reactive transformation of the intermediate layer to a gastric juice-resistant layer in the gastric juice acidic medium. The closer the pH value of the partially neutralized intermediate layer lies to 5.5, the faster this occurs.

Thus, it clearly emerges from all experiments in Examples 1 to 3 that according to the invention a medicament with surprisingly improved stability is obtained in comparison to those of the state of the art. The stability behaviour is demonstrated especially at increased temperature and humidity (trituration experiments) but also under intensified storage conditions of 40° C. and 75% r.H of pellets.

EXAMPLE 4

Release Behaviour of Various Pellet Formulas:

Essential for the good bio-availability of the active ingredient is its release as quickly as possible in the upper small intestine region, i.e. in a weakly acid/neutral environment. To investigate the release behaviour pellets with various formulas were introduced into an aqueous medium with a pH value of 5.8 as an in vitro model for the upper small intestine (artificial intestinal fluid) and the Omeprazole released under stirring into the surroundings was determined as a function of time with HPLC (analogously to the Pharmacopia)

The examined pellet formulas and the release results are reproduced in Table 4:

TABLE 4

| | | Released Omeprazole [%] release period | | |
|---|---|---|---|---|
| Batch | Pellet formula | 30 min | 45 min | 60 min |
| | according to the invention | | | |
| 4a | Omeprazole-Core + Adjuvant*, IL.: 3% E. L 100-55 pH 7.0 gjr: 30% E. L 100-55 | 72 | 84 | 89 |
| 4b | Omeprazole-Core + Adjuvant*, IL.: 3% E. L 100-55 pH 6.0 gjr: 30% E. L 100-55 | 40 | 81 | 88 |
| | comparative examples | | | |
| 4c | Omeprazole-Core + Adjuvant*, no IL. gjr: 30% E. L 100-55 | 3 | 5 | 8 |
| 4d | Omeprazole-Core + Adjuvant*, no IL gjr: 20% E. L 100-55 | 13 | 37 | 59 |

*Adjuvant: Mannite, HPC, sodium lauryl sulfate
IL: Intermediate layer
E: Eudragit (percent by weight with respect to the core)
gjr: gastric juice-resistant (layer) (percent by weight with respect to the core)

Figure 3:
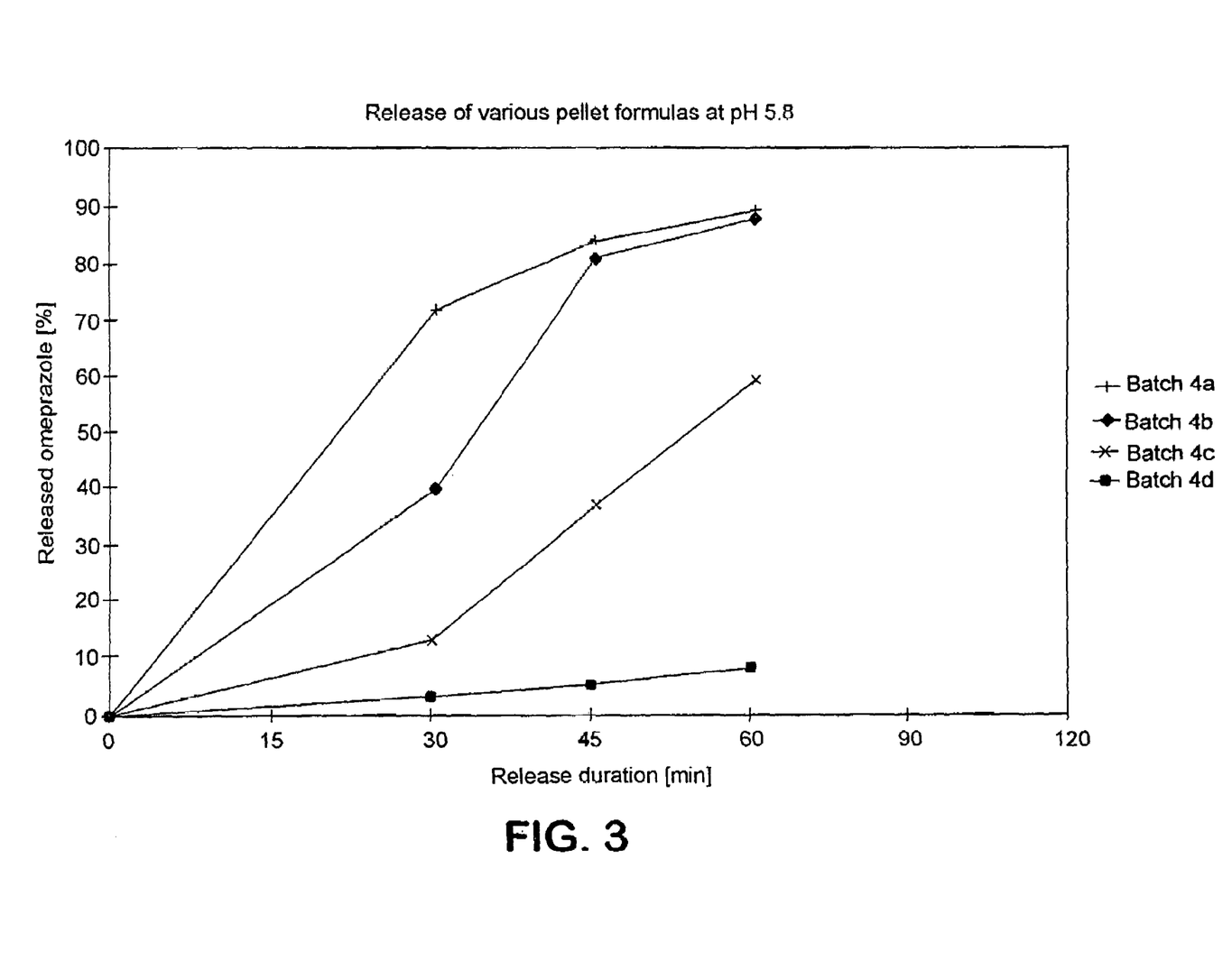
FIG. 3 shows the release of various pellet formulas at pH 5.8.

FIG. 3 shows a graphic representation of the result.

The thickness of the outer enteric layer with pellet batches 4 a, b and c is each the same (30% by weight with respect to the pellet core, corresponding to ca. 40 μm). Despite this, batches 4a and 4b provided with the reactive intermediate layer according to the invention demonstrate a clearly quicker dissolution in artificial intestinal fluid than when no intermediate layer (batch 4c) is present. This is also still the case when the enteric coating layer is more thinly formed (batch 4b, 206 by weight with respect to the pellet core, corresponding to ca. 30 μm). This permits the thickness of the outer enteric layer in the medicaments according to the invention to be further increased which offers an improved medicament safety in comparison to known preparations without negatively influencing release behaviour—which was not to be expected.

EXAMPLE 5

Improved Stability of the Active Ingredient-containing Core:

Granulates of Omeprazole with various adjuvants were produced in a mortar. After open storage over 32 days at 40° C. and 75% relative humidity, the residual content of Omeprazole as well as the appearance of degradation product were determined with HPLC. $Na_2HPO_4$ buffering in an alkaline environment, Texapon, lactose, L-HPC, microcrystalline cellulose and mannite (batch 5b) as well as a combination of these adjuvants without $Na_2HPO_4$ (batch 5c) were employed as adjuvants. These batches were compared with an Omeprazole granulate which aside from the active ingredient only contained HCP and mannite (batch 5a). The results are reproduced in Table 5.

TABLE 5

| Batch | Formula (Granulate) Storage conditions Storage duration | Gehalt Omeprazole [precent by weight] 40° C./75% rel. Feuchte after production. | | Degradation product of Omeprazole [area-%] after production. | |
|---|---|---|---|---|---|
| | | | 32 days | | 32 days |
| | preferred according to the invention | | | | |
| 5a | Omeprazole*, Mannite HPC | 100 ⇨ | 100 | <0.1 ⇨ | <0.5 |
| | Referenzbeispiel | | | | |
| 5b | Omeprazole adjuvants $Na_2HPO_4$ | 100 ⇨ | 100 | <0.1 ⇨ | <0.5 |
| 5c | Omeprazole adjuvants without $Na_2HPO_4$ | 100 ⇨ | 72 | <0.1 ⇨ | ca.30 |

As expected, the Omeprazole granulate without alkaline reacting additive (batch 5c) demonstrated a clearly deteriorated storage stability compared to an Omeprazole granulate with $Na_2HPO_4$ as an additive (batch 5b). Thus, the Omeprazole content decreases to 72%; ca. 30 area-% degradation product arises. Surprisingly, an Omeprazole granulate with mannite and hydroxypropylcellulose as the only adjuvants, particularly without alkaline reacting additives (batch 5a), also has an outstanding storage stability. Therefore, in the preferred medicament according to the invention, it is not necessary and is also not preferred to use alkaline reacting adjuvants or Omeprazole salts in the core because, if necessary, alkaline substances diffusing from the core into the reactive intermediated layer can be hindered by the "self-repair mechanism" as illustrated above.

EXAMPLE 6

Production of Medicaments According to the Invention:

FORMULA EXAMPLES

| Medicament A Core: | |
|---|---|
| Omeprazole | 210.00 g |
| Mannite | 781.60 g |
| Hydroxypropylcellulose | 3.30 g |
| Sodium lauryl sulfate | 5.00 g |
| Intermediate layer: | |
| Eudragit ® L100-55 neutralized to pH 7.0 with NaOH | 50.00 g |
| Triethyl citrate | 5.00 g |
| Gastric juice-resistant (outer) layer: | |
| Eudragit ® L100-55 | 300.00 g |
| Triethyl citrate | 30.00 g |
| Mikronized Talcum | 150.00 g |
| Medicament B Core: | |
| Omeprazole | 210.00 g |
| Mannite | 781.60 g |
| Hydroxypropylcellulose | 3.30 g |
| Sodium lauryl sulfate | 5.00 g |
| Intermediate layer: | |
| Eudragit ® L 100-55 neutralized to pH 5.5 with NaOH | 50.00 g |
| Triethyl citrate | 5.00 g |
| Talcum | 15.00 g |
| Gastric juice-resistant (outer) layer: | |
| Eudragit ® L100-55 | 400.00 g |
| Triethyl citrate | 40.00 g |
| Micronized talcum | 200.00 g |

The pre-weighed components Omeprazole, mannite and sodium lauryl sulfate are placed in a mixer and mixed. A granulation liquid of hydroxypropylecellulose dissolved in isopropanol is slowly added to the pre-mixed components in the mixer under constant stirring. If necessary, further isopropanol can be added for better pellet formation. The mixing time amounts to 10 to 20 minutes until the majority of the pellets have a desired average size of ca. 1000 μm.

The moist pellets are dried in a dryer at ca. 60° C. for ca. 40 min. Pellets with a diameter of <700 μm or >1200 μm are sieved out.

The pellets are obtained in a fluidized state during which at first a coating dispersion I and subsequently a coating dispersion II is sprayed on to the pellets with a constant rate.

For production of the coating-dispersion I, purified water is filled into a stainless steel vessel and sodium hydroxide is dissolved in the water. The sodium hydroxide solution is added to micronized talcum under stirring, a Eudragit® dispersion is then slowly added to the sodium hydroxide/talcum dispersion under stirring whereby clumps and foam formation must be avoided. After addition of triethyl citrate to the dispersion, stirring continued for at least 15 minutes whereby the pH value is adjusted to pH 7.0 and/or pH 5.5 with sodium hydroxide solution. The dispersion must be continuously stirred during the formation of the coat.

For production of the coating dispersion II, micronized talcum is dispersed in purified water. Subsequently, the aqueous dispersion obtained in this manner is added to the Eudragit® dispersion under stirring whereby the appearance of clumps or foam must be avoided. After addition of triethyl citrate, the dispersion is further stirred for at least 15 min. The Omeprazole pellets are then transferred into a coating apparatus and laminated at first with the coating dispersion I and then with the coating dispersion II. The finished Omeprazole pellets are filled into hard gelatine capsules.

EXAMPLE 7

In-vitro Experiments on Chemical Stability of the Medicament According to the Invention:

It is known that Omeprazole loses its effectiveness with longer storage which is traceable to a degradation of the active ingredient. This chemical degradation of Omeprazole can be reduced to a minimum by applying suitable protection layers.

It could be demonstrated in stability tests under stress conditions (40° C./75% rel. humidity) that the medicament according to the invention loses less than 2 percent by weight on active ingredient (average value of each of three content determinations) when stored in closed, brown screw-cap vials for 4 weeks. In contrast, a commercial product (Antra 20, VD5672-A01) lost more than 80 percent by weight on active ingredient under identical conditions in the same time period (see Table 6).

TABLE 6

| Medicament (batch) | Omeprazole residual content after 12 week storage at 40° C./75% r.H. in a closed, screw-cap vial (percent by weight) |
|---|---|
| according to the ivention | |
| 6a | 98.9 |
| 6b | 98.3 |
| 6c | 99.3 |
| commercial product | |
| 6d | 16.2 |

In further stability tests under long-term and stress conditions (25° C./60% r.H; 30° C./60% r.H; 40° C./75% r.H), it could be demonstrated that the medicament according to the invention loses less than 5 percent by weight on active ingredient (average value of each of three content determinations) when stored in the primary package for 12 weeks. The results are depicted in Table 7.

TABLE 7

| Medicament (batch) storage conditions | Omeprazole content after 12 Weeks storage percent by weight | | |
|---|---|---|---|
| | 25° C./60% r.H. | 30° C./60% r.H. | 40° C./75% r.H. |
| 7a | 98.9 | 97.9 | 97.8 |
| 7b | 99.1 | 97.8 | 95.3 |
| 7c | 100.5 | 100.3 | 98.0 |

The results clearly demonstrate that no significant decrease in content from the starting value was determined with the medicament according to the invention.

EXAMPLE 8

Determination of the Gastric-juice-resistance:

For determining the gastric-juice-resistance, samples of the inventive medicament according to Example 6 were subjected to an in vitro test. Thereby, each sample, which was found in a basket at pH 1.2 and a temperature of 37° C. as well as 100 rpm of the basket, was left in the acidic medium for 120 minutes and subsequently the sample was analysed as to the remaining active ingredient content. The values obtained thereby are summarized in Table 8. All values show that no significant degradation from the starting values resulted under the selected conditions.

TABLE 8

| Medicament (batch) | Omeprazole residual content percent by weight |
|---|---|
| according to the ivention | |
| 8a | 98.4 |
| 8b | 98.9 |
| 8c | 96.0 |

EXAMPLE 9

In Vitro Experiments on Active Ingredient Release:

For the following experiments, an inventive medicament according to Example 6 was also examined. The respective sample, which was found in a basket, was exposed to a medium (1000 ml) of pH 1.2 for 120 minutes at 37° C.

After the above-mentioned residence time in acidic medium, this was replaced by an alkali medium (pH 6.8, phosphate buffered) and the samples were left therein for a time period of 5, 10, 15, 20, 30, 60 minutes respectively. After the mentioned time intervals, analysis as to the least active ingredient was carried out.

Figure 4:
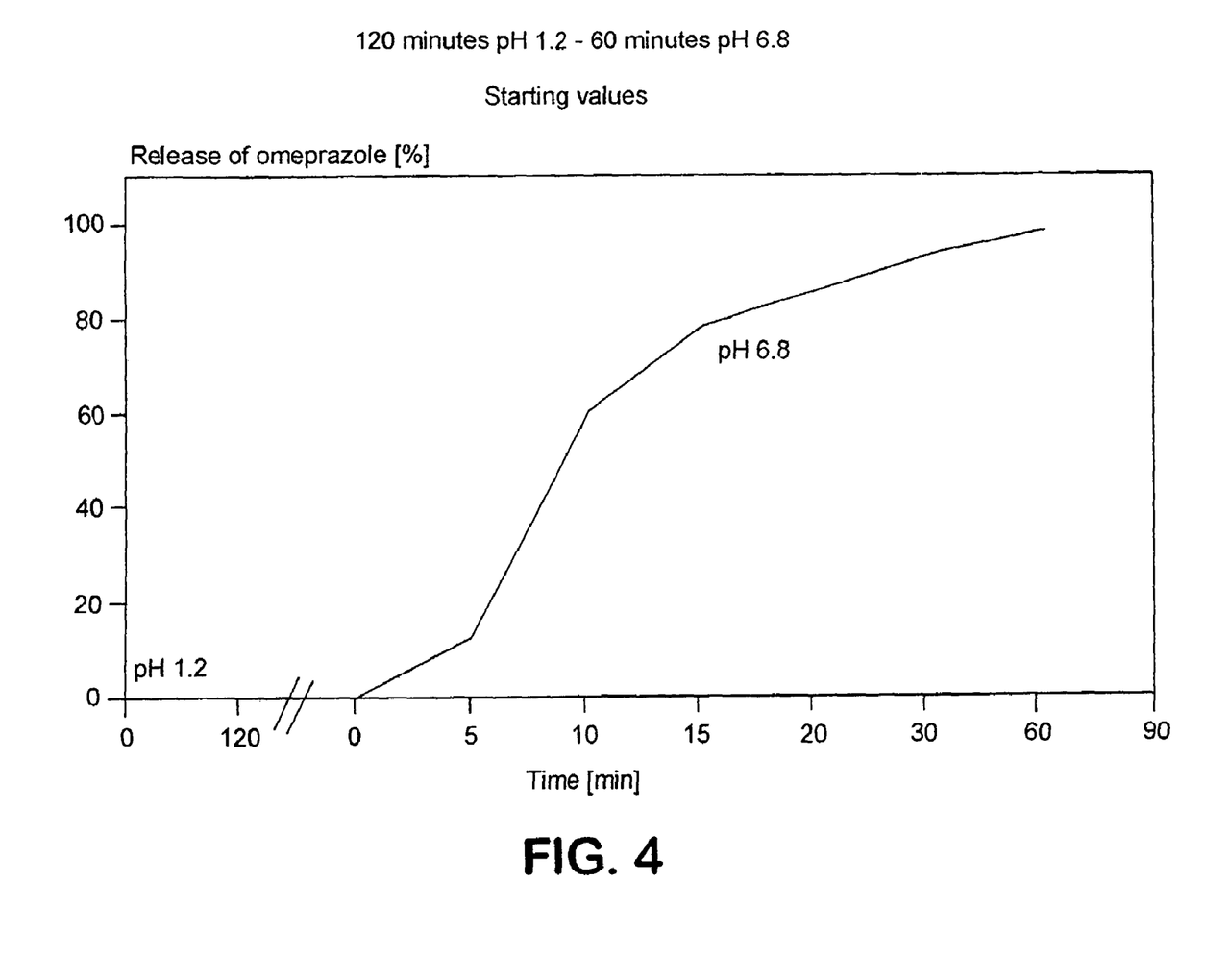
FIG. 4 describes the release of Omeprazole pellets exposed to a pH of 1.2 for 120 minutes and a pH of 6.8 for 60 minutes.
Figure 5:
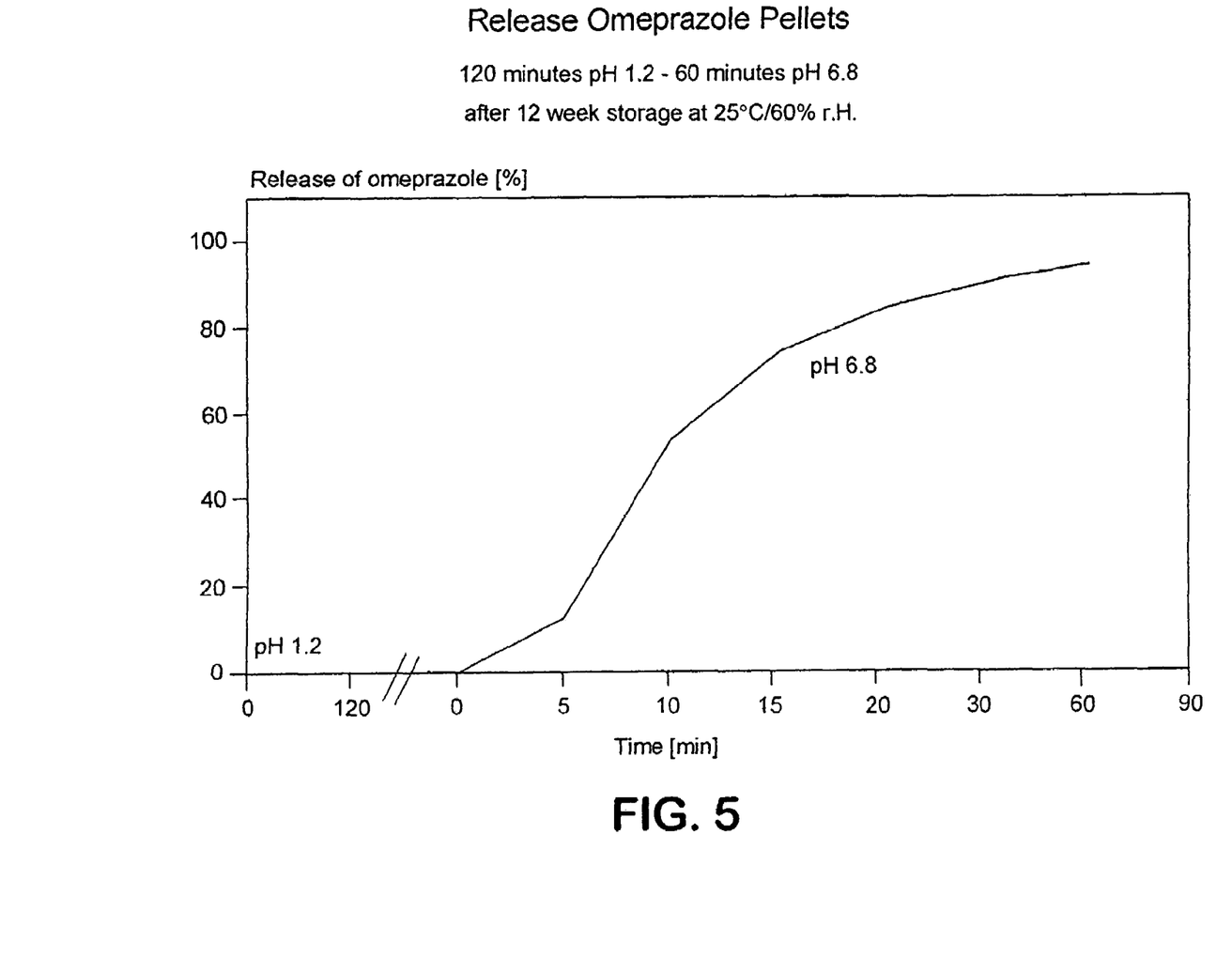
FIG. 5 describes the release of Omeprazole pellets exposed to a pH of 1.2 for 120 minutes and a pH of 6.8 for 60 minutes after 12 weeks of storage at 30 degree C. and 60% relative humidity.
Figure 6:
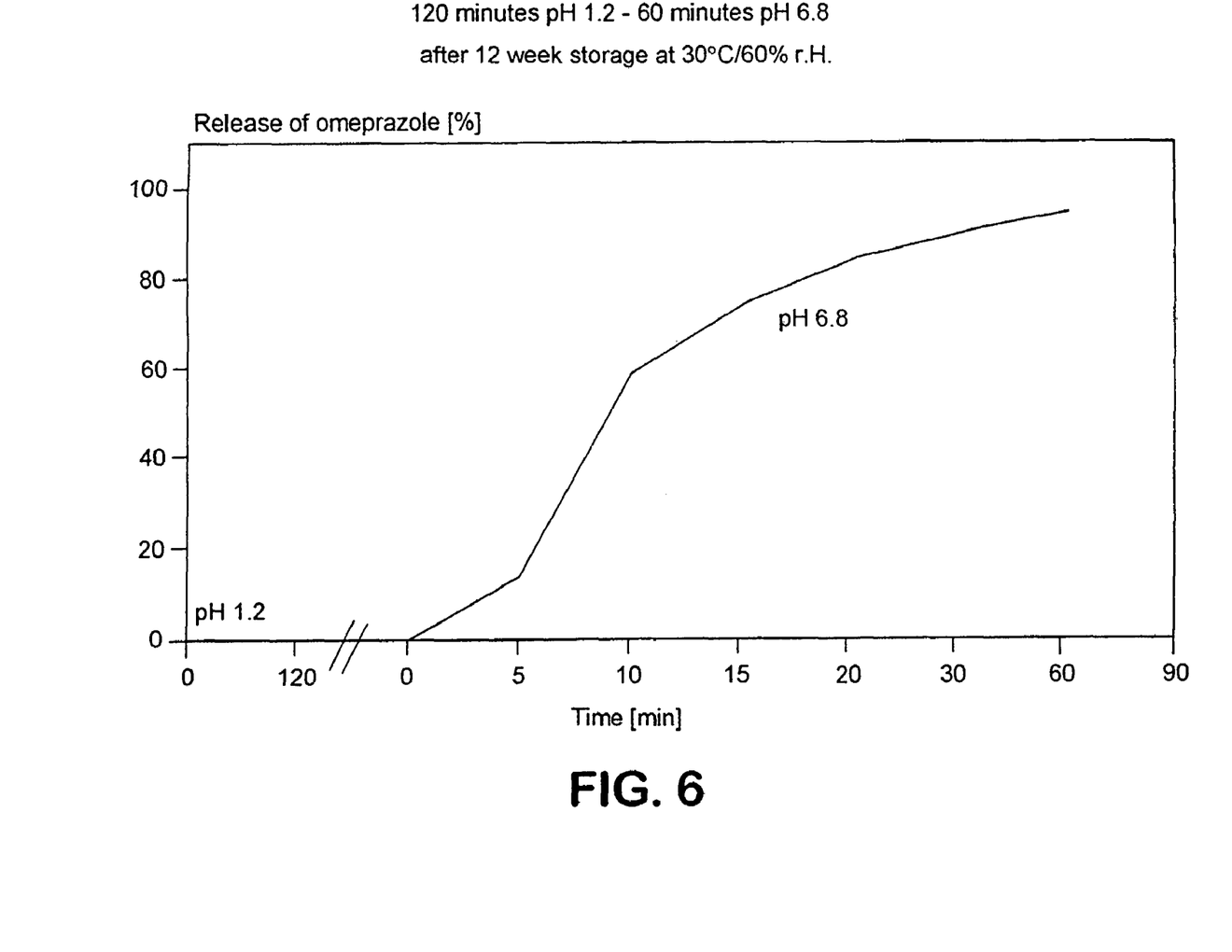
FIG. 6 describes the release of Omeprazole pellets exposed to a pH of 1.2 for 120 minutes and a pH of 6.8 for 60 minutes after 12 weeks of storage at 30 degree C. and 60% relative humidity.
Figure 7:
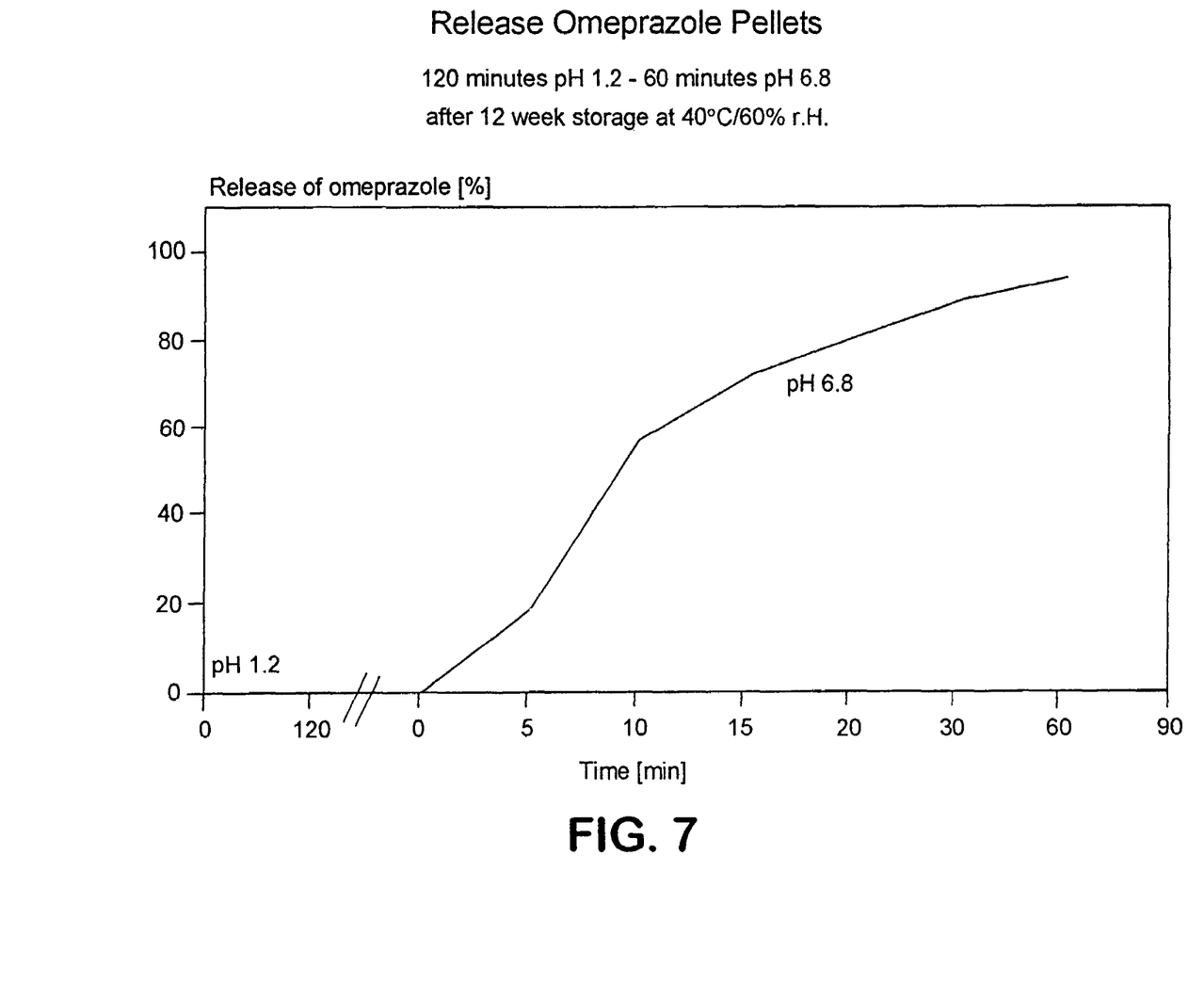
FIG. 7 describes the release of Omeprazole pellets exposed to a pH of 1.2 for 120 minutes and a pH of 6.8 for 60 minutes after 12 weeks of storage at 40 degree C. and 60% relative humidity.

The determination of the in vitro active ingredient release occurred on samples which before their storage (FIG. 4) and after 12 week storage at 25° C./60' r.H. (FIG. 5), at 30° C./60% r.H. (FIG. 6) and 40° C./75% r. H. (FIG. 7). The medicaments were previously filled in the designated packaging. The obtained values are represented for the respective batches according to the invention in FIGS. 4 to 7 and show that the release is stable over the storage time.

EXAMPLE 10

Combination Preparation Omeprazole and Diclofenac:

Capsule Formulation C:

A capsule contains 210mg Diclofenac pellets corresponding to 75 mg Diclofenac-Na and 160 mg Omeprazole pellets corresponding to 20 mg Omeprazole. The Diclofenac pellets as well as the Omeprazole-pellets were produced according to the method of production according to Example 6.

Capsule Formulation D

A capsule contains 420 mg Diclofenac pellets corresponding to 150 mg Diclofenac-Na and 160 mg Omeprazole pellets corresponding to 20 mg Omeprazole which were produced according to Example 6. The Diclofenac pellets were produced according to the method given in EP 0 348 808.

The invention claimed is:

1. A method of inhibiting gastric acid secretion which method comprises administering to a subject in need thereof a therapeutically effective amount of a stable medicament for oral administration which comprises:
    (a) a core which contains an active ingredient selected from the group consisting of Omeprazole, Lansoprazole, and Pantoprazole, together with pharmaceutical adjuvants;
    (b) an intermediate layer applied onto the core; and
    (c) a gastric juice-resistant outer layer, wherein the intermediate layer is a reactive layer comprising a gastric juice-resistant polymeric layered material partially neutralized with alkali and having cation exchange capacity.

2. The method according to claim 1, wherein the alkali is selected from the group consisting of sodium hydroxide and potassium hydroxide.

3. The method according to claim 1, wherein the pharmaceutical adjuvant is selected from the group consisting of mannite and hydroxypropylcellulose.

4. The method according to claim 1, wherein the core further comprises a tenside.

5. The method according to claim 4, wherein the tenside is selected from the group consisting of sodium lauryl sulfate, sorbitan fatty acid ester and polyethylene sorbitan fatty acid ester.

6. The method according to claim 1, wherein the core is present in the form of pellet cores, tablets, microtablets, or as a granulate.

7. The method according to claim 1, wherein the polymeric layered material is partially neutralized to a pH range of about 5.5 to about 7.0.

8. The method according to claim 7, wherein the polymeric layered material is selected from the group consisting of a partially neutralized copolymer of methacrylic acid and ethylacrylate, a copolymer of methacrylic acid and methylmethacrylate, hydroxypropylmethylcellulose phthalate (HPMCP), and cellulose acetate phthalate (CAP).

9. The method according to claim 1, wherein the intermediate layer further comprises a plasticizer.

10. The method according to claim 9, wherein the plasticizer is selected from the group consisting of triethyl citrate, acetyltriethyl citrate, acetylated monoglycerides, propylene glycol, and polyethylene glycols.

11. The method according to claim 1, wherein the intermediate layer forms a gel layer with penetration of protons through the outer layer.

12. The method according to claim 1, wherein the intermediate layer possesses a thickness of from about 5 to about 30 μm.

13. The method according to any one of claims 1 to 12, wherein the gastric juice-resistant outer layer in (c) contains a copolymer selected from the group consisting of copolymers of methacrylic acid and ethylacrylate, copolymers of methacrylic acid and methylmethacrylate, hydroxypropylmethylcellulose phthalate (HPMCP), and cellulose acetate phthalate (CAP).

14. The method according to claim 13, wherein the gastric juice-resistant outer layer contains compounds selected from the group consisting of pharmaceutically acceptable antitacking agents, dispersion agents, pigments and colorants.

15. The method according to claim 14, wherein the antitacking agent is talcum.

16. The method according to claim 1, wherein the gastric juice-resistant outer layer has a layer of thickness from about 20 to about 60 μm.

17. The method according to claim 1 wherein the medicament for oral administration comprises:
   (a) a core which contains an active ingredient selected from the group consisting of Omeprazole, Lansoprazole, and Pantoprazole, together with mannite and hydroxypropylcellulose as adjuvants without alkaline additives;
   (b) a reactive intermediate layer applied on the core with a thickness from about 5 to about 30 μm of a copolymer of methacrylic acid and ethylacrylate partially neutralized with sodium hydroxide to a pH range of about 5.5 to about 7.0; and
   (c) a gastric juice-resistant outer layer of a copolymer of methacrylic acid and ethylacrylate with a thickness from about 30 to about 60 μm.

18. The method according to claim 1, wherein the intermediate layer is formed as a plurality of single layers.

19. The method according to claim 1, wherein the gastric juice-resistant outer layer is formed as a plurality of single layers.

20. The method according to claim 1, wherein the pH transition at the border of the gastric juice-resistant outer layer to the reactive intermediate layer is formed as a gradient.

21. The method according to claim 1 further comprising the administration of Diclofenac.

22. The method according to claim 21, wherein the Diclofenac is present as a formulation which comprises:
   (a) a Diclofenac-containing core together with adjuvants;
   (b) a reactive intermediate layer of gastric juice-resistant polymeric layered material partially neutralized with alkali; and
   (c) a gastric juice-resistant outer layer.

23. The method according to claim 21, wherein the Diclofenac is present as a pellet formulation comprising a mixture of gastric juice-resistant coated pellets and retarded, permeable pellets.

* * * * *

UNITED STATES PATENT AND TRADEMARK OFFICE
CERTIFICATE OF CORRECTION

PATENT NO. : 7,276,253 B2  
APPLICATION NO. : 11/502830  
DATED : October 2, 2007  
INVENTOR(S) : Hesse et al.

It is certified that error appears in the above-identified patent and that said Letters Patent is hereby corrected as shown below:

Col. 4:  
Line 14: "30 degree C." should read --25 degree C.--

Signed and Sealed this

Fifth Day of August, 2008

JON W. DUDAS  
*Director of the United States Patent and Trademark Office*